US007655008B2

(12) United States Patent
Lenke et al.

(10) Patent No.: US 7,655,008 B2
(45) Date of Patent: Feb. 2, 2010

(54) METHODS AND INSTRUMENTS FOR SPINAL DEROTATION

(75) Inventors: Lawrence G. Lenke, St. Louis, MO (US); John Stewart Young, Memphis, TN (US); Douglas D. Kave, Byhalia, MS (US)

(73) Assignee: Warsaw Orthopedic, Inc.

( * ) Notice: Subject to any disclaimer, the term of this patent is extended or adjusted under 35 U.S.C. 154(b) by 413 days.

(21) Appl. No.: 11/350,915

(22) Filed: Feb. 9, 2006

(65) Prior Publication Data

US 2007/0213716 A1   Sep. 13, 2007

(51) Int. Cl.
*A61B 17/56* (2006.01)
*A61B 17/58* (2006.01)
*A61B 17/70* (2006.01)
*A61B 17/88* (2006.01)

(52) U.S. Cl. .................. 606/60; 606/86 A; 606/90; 606/246; 606/251; 606/252; 606/253; 606/254; 606/255; 606/256; 606/257; 606/266; 606/279; 606/914

(58) Field of Classification Search .................. 606/61, 606/86, 104, 105, 264, 916, 60, 86 A, 90, 606/246, 251–257, 266, 279, 914; 623/19.13
See application file for complete search history.

(56) References Cited

U.S. PATENT DOCUMENTS

| 4,409,968 A | 10/1983 | Drummond |
| 4,505,268 A | 3/1985 | Sgandurra |
| 5,020,519 A | 6/1991 | Hayes et al. |
| 5,102,412 A | 4/1992 | Rogozinski |
| 5,181,917 A | 1/1993 | Rogozinski |
| 5,196,013 A | 3/1993 | Harms et al. |
| 5,261,907 A | 11/1993 | Vignaud et al. |
| 5,281,223 A | 1/1994 | Ray |
| 5,385,565 A | 1/1995 | Ray |
| 5,425,732 A | 6/1995 | Ulrich |
| 5,437,669 A | 8/1995 | Yuan et al. |
| 5,478,340 A | 12/1995 | Kluger |
| 5,531,747 A | 7/1996 | Ray |
| 5,545,166 A | 8/1996 | Howland |
| 5,591,165 A | 1/1997 | Jackson |
| 5,632,744 A | 5/1997 | Campbell, Jr. |
| 5,649,926 A | 7/1997 | Howland |
| 5,672,175 A | 9/1997 | Martin |
| 5,702,392 A | 12/1997 | Wu et al. |
| 5,702,457 A * | 12/1997 | Walch et al. ............. 623/19.13 |
| 5,704,937 A | 1/1998 | Martin |
| 5,707,371 A | 1/1998 | Metz-Stavenagen |

(Continued)

FOREIGN PATENT DOCUMENTS

DE    87 12 943 U1    11/1987

(Continued)

*Primary Examiner*—Thomas C Barrett
*Assistant Examiner*—Sameh Boles

(57) ABSTRACT

Derotation instrument assemblies and systems are provided to facilitate positioning one or more vertebrae of a spinal column into a desired alignment. The instrument assemblies and systems include implant holders engageable to respective implants engaged to vertebrae of the spinal column, transverse bridges to connect implant holders associated with a particular vertebra, and inter-level linking assemblies to connect instrument assemblies associated with different vertebrae. Derotation handles can be provided on the implant holders to facilitate application of the alignment forces, while the assemblies distribute the corrective forces to the connected implants and vertebrae.

41 Claims, 14 Drawing Sheets

U.S. PATENT DOCUMENTS

| | | | |
|---|---|---|---|
| 5,733,284 A | 3/1998 | Martin | |
| 5,797,910 A | 8/1998 | Martin | |
| 5,814,046 A | 9/1998 | Hopf | |
| 6,015,409 A | 1/2000 | Jackson | |
| 6,090,113 A | 7/2000 | LeCouedic et al. | |
| 6,171,311 B1 * | 1/2001 | Richelsoph | 606/252 |
| 6,251,112 B1 * | 6/2001 | Jackson | 606/916 |
| 6,402,753 B1 * | 6/2002 | Cole et al. | 606/62 |
| 6,458,131 B1 | 10/2002 | Ray | |
| 6,511,484 B2 * | 1/2003 | Torode et al. | 606/104 |
| 6,565,568 B1 | 5/2003 | Rogozinski | |
| 6,605,088 B1 | 8/2003 | St. Onge et al. | |
| 6,648,888 B1 | 11/2003 | Shluzas | |
| 6,749,613 B1 | 6/2004 | Conchy et al. | |
| 6,755,828 B2 | 6/2004 | Shevtsov et al. | |
| 7,004,947 B2 * | 2/2006 | Shluzas et al. | 606/105 |
| 2003/0144665 A1 * | 7/2003 | Munting | 606/61 |
| 2003/0225408 A1 | 12/2003 | Nichols et al. | |
| 2004/0034350 A1 | 2/2004 | St. Onge et al. | |
| 2004/0172022 A1 | 9/2004 | Landry et al. | |
| 2004/0249378 A1 * | 12/2004 | Saint Martin et al. | 606/61 |
| 2005/0033291 A1 | 2/2005 | Ebara | |
| 2005/0033299 A1 * | 2/2005 | Shluzas | 606/61 |
| 2005/0149036 A1 | 7/2005 | Varieur et al. | |
| 2005/0149053 A1 | 7/2005 | Varieur et al. | |
| 2005/0159757 A1 | 7/2005 | Shluzas et al. | |
| 2005/0171540 A1 | 8/2005 | Lim et al. | |
| 2005/0182400 A1 * | 8/2005 | White | 606/61 |
| 2005/0245928 A1 | 11/2005 | Colleran et al. | |
| 2006/0106380 A1 | 5/2006 | Colleran et al. | |
| 2007/0093846 A1 * | 4/2007 | Frigg et al. | 606/90 |
| 2007/0161989 A1 | 7/2007 | Heinz et al. | |
| 2007/0173827 A1 * | 7/2007 | Morrison et al. | 606/61 |
| 2007/0213715 A1 * | 9/2007 | Bridwell et al. | 606/61 |

FOREIGN PATENT DOCUMENTS

| | | |
|---|---|---|
| EP | 0 528 177 A2 | 2/1993 |
| EP | 0 602 351 A1 | 6/1994 |
| EP | 1 269 930 A2 | 1/2003 |
| WO | WO 90/02527 | 3/1990 |
| WO | WO 91/06254 | 5/1991 |
| WO | WO 02/094114 A1 | 11/2002 |
| WO | WO 2005/058141 A2 | 6/2005 |

* cited by examiner

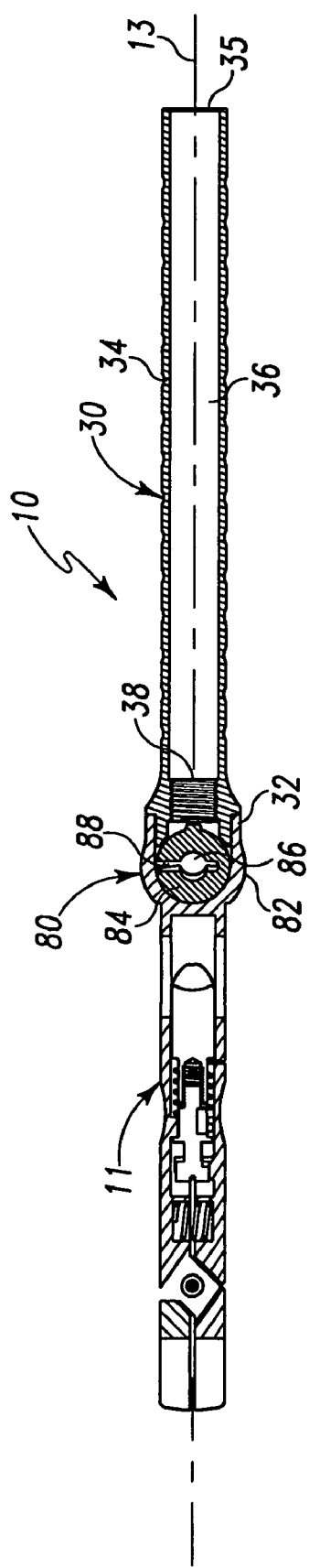
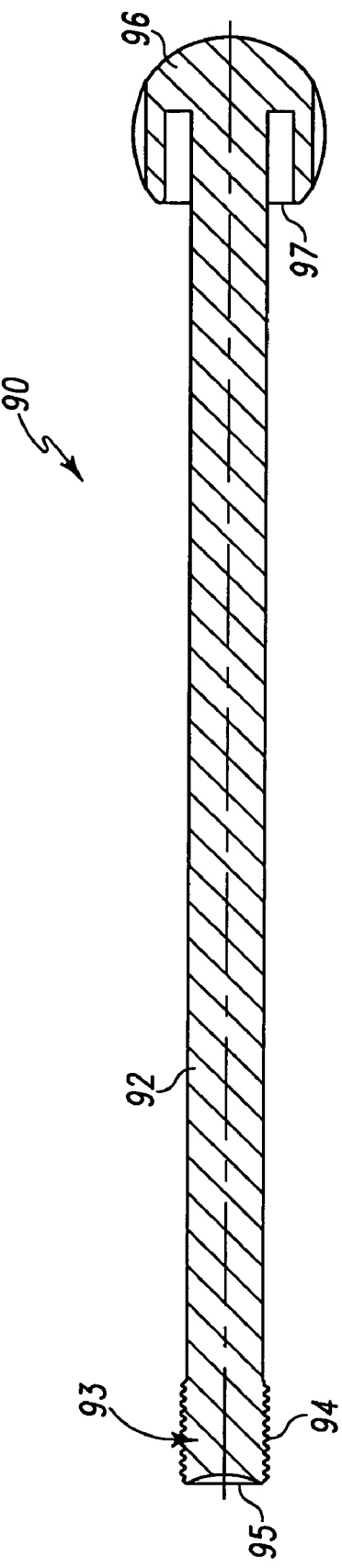
Fig. 7
Fig. 8

METHODS AND INSTRUMENTS FOR SPINAL DEROTATION

BACKGROUND

Surgical correction of the positioning and alignment of one or more vertebrae in the spinal column can be desired to address various pathologies and conditions of patients. However, such repositioning and re-alignment can be time-consuming, cumbersome, and potentially difficult to achieve during a surgical procedure. For example, the alignment of multiple vertebral levels can require manipulation of instrumentation at each level to achieve the desired results. Forces applied to the vertebral body need to be controlled to minimize stresses on the vertebral bodies and implants. Furthermore, the alignment at one level should be maintained while other levels are aligned. In addition, the instrumentation employed to achieve the alignment can hinder placement of stabilization constructs that post-operatively maintain the corrected positioning and alignment achieved during surgery.

Therefore, instruments, methods and systems that facilitate surgical correction of the alignment and positioning of a vertebra or vertebrae of the spinal column would be desirable. Furthermore, instruments, methods and systems that facilitate placement of stabilization constructs that post-operatively maintain the corrected vertebra or vertebrae are also desirable. In addition, instruments, methods and systems that facilitate control of the stress exerted on implants and vertebrae to which the implants are attached would be desirable.

BRIEF DESCRIPTION OF THE DRAWINGS

FIG. 7 is a longitudinal section view of one embodiment implant holder.

FIG. 8 is a longitudinal section view of a locking member useable with the implant holder of FIG. 7.

DETAILED DESCRIPTION OF THE ILLUSTRATED EMBODIMENTS

Figure 1:
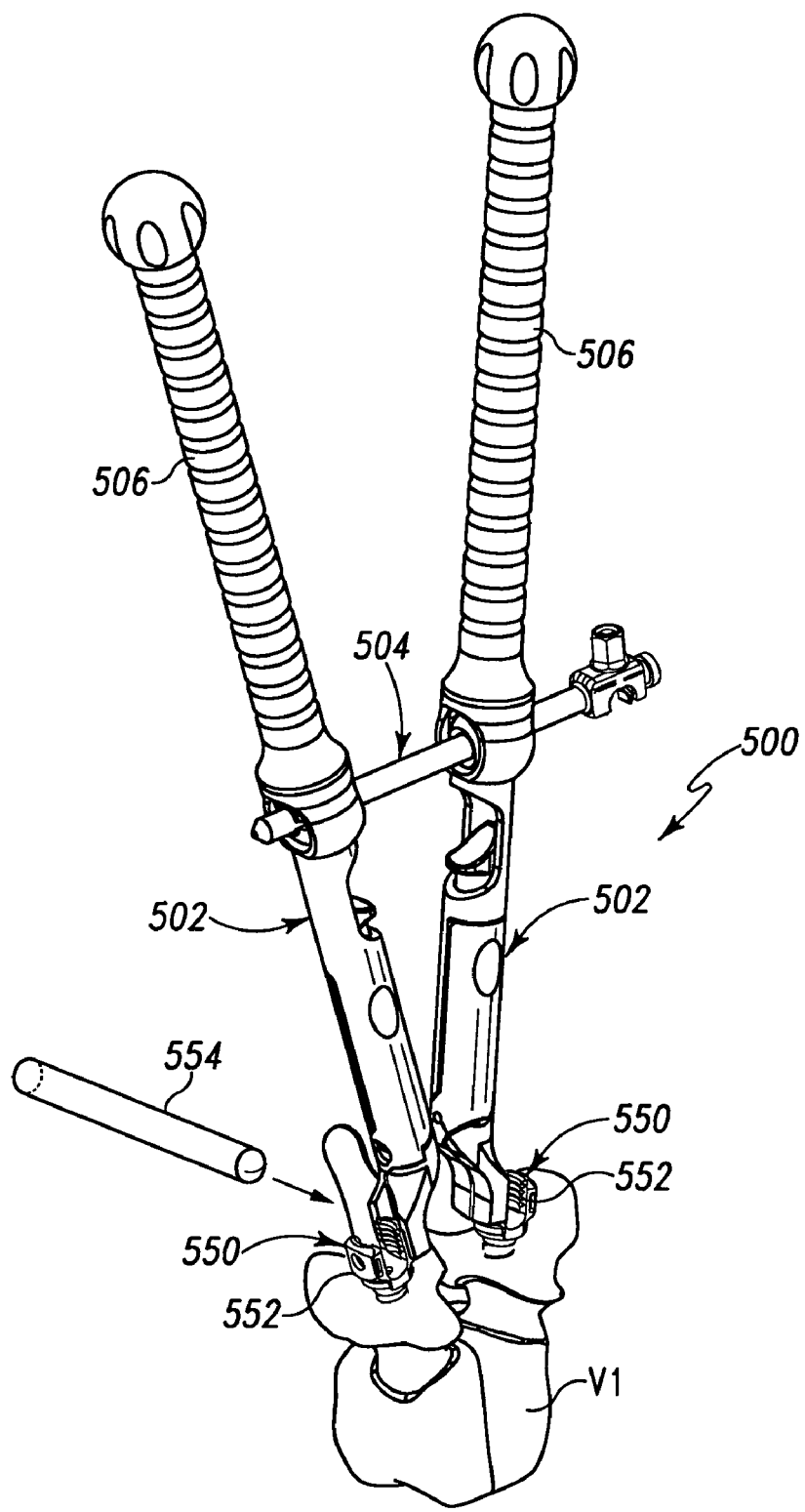
FIG. 1 is a perspective view of a derotation instrument assembly coupled to implants engaged to a vertebra.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Spinal derotation instrumentation is provided to affect one or more derotation maneuvers on a scoliotic spine or on a spine having one or more displaced, misaligned or curved vertebral levels. Specifically, a derotation instrument assembly is attached to at least one vertebral body, with the assembly including at least a pair of bone implants anchored to the vertebral body along the left and right sides of the spinal column; an elongate implant holder removably attached to a head portion of each of the bone implants; a transverse bridge interconnecting the proximal end portions of the implant holders; and a primary handle extending from each of the implant holders proximally of the location in which the transverse bridge is engaged to the respective implant holder. The handles are provided for manipulation by the surgeon, and manipulation forces exerted on one handle are distributed to each implant/vertebra interface by the transverse bridge and other implant holder.

The derotation handles can extend proximally and axially from a distal clamping portion of each of the implants. In one embodiment, only one of the implant holders includes a derotation handle, and the transverse bridge is engaged directly to the proximal end of the other implant holder. The derotation handle or handles may be formed unitarily with the distal clamping portion of the respective implant holder, or may be threadingly or otherwise suitably removably engaged to the distal clamping portion of the respective implant holder to allow for selective attachment and removal.

The bone implants can be configured as pedicle screws, with each screw having a head portion which includes a pair of arms defining a U-shaped channel for receiving a spinal rod, and with the arms defining internal threads for threadingly receiving a set screw for capturing the spinal rod within the U-shaped channel. The screw can be uni-axial, or multi-axial so that the head can pivot relative to the bone engaging portion. In the illustrated embodiment, the head portions of the screws are configured to receive stabilization element either through a top opening between the pair of arms or to receive an end of the stabilization element as it is passed through the head in an end-wise manner. In another embodiment, the head portion of the screws opens to a side so that the stabilization element can be side-loaded therein. Other embodiments contemplate any suitable type of implant that can be engaged to a vertebra and coupled to an elongated stabilization element.

The elongate implant holders can each include a distal clamp portion with a distal end portion configured for selective clamping to either arm of the screw head portion. In another embodiment, the implant holder clamps across both arms of the implant. In one specific embodiment, the implant holder includes a clamp portion having a tubular body extending the length of the implant holder and a clamping arm pivotally attached to the tubular body via a pivot pin. A spring may be included for biasing the clamping arm toward an open position along with a releasable latching mechanism to releasably capture the arm of the screw head portion between the distal end portions of the tubular body and the clamping arm. The implant holder may also include a release button to selectively release the tubular body and the clamping arm from the arm of the screw head portion. The implant holder can include a length so that at least its proximal handle is positioned outside the patient through the wound or incision in which the vertebrae are accessed.

The location of the implant holder between the distal clamping end and the proximal handle (or the proximal end of the implant holder if a handle is not provided) can include a joint to facilitate attachment of the transverse bridge at any one of a number of angular orientations relative the implant holder. The joint can be of any suitable configuration, and specific embodiments contemplate a spherical segment unitarily joined with the implant holder, a ball and socket arrangement, or a ball end, for example. The joint of at least one of the implant holders associated with a vertebra can be engaged to the transverse bridge via a clamping mechanism or interference fit that allows at least one implant holder to be engaged to the connecting member at any one of a number of positions along the connecting member. Such engagement between the implant holders and the transverse bridge allows for variable lateral adjustment and variable angular adjustment of the implant holders relative to the transverse bridge. In still another embodiment, the transverse bridge can connect implant holders engaged to respective ones of two or more vertebrae, and extend across the spinal midline to link the implant holders to one another.

In one embodiment, the transverse bridge is configured as a plate defining an elongate slot extending therethrough. One end of the plate is engaged about a spherical joint of one implant holder, and the slot includes a number of recesses or scalloped areas that can each receive a spherical joint of the other implant holder in any one of a plurality of angular orientations. In another embodiment, the transverse bridge includes a rod-like member positioned through ball-joint mechanisms of the implant holders. In another embodiment, the connecting member is engaged to clamp assemblies that are engaged to the implant holder.

In instances requiring derotation across multiple vertebral levels, a derotation instrument assembly may be attached to respective ones of the multiple vertebral bodies requiring derotation, with the derotation instrument assemblies being interconnected by an inter-level linking assembly coupled between the individual derotation instrument assemblies. As a result, the surgeon may manipulate an integrated frame assembly to affect derotation across multiple vertebral levels, rather than separately manipulating several derotation instrument assemblies to effect derotation at each individual vertebral level. The transverse bridges can be releasably coupled to the implants holders associated with each of the vertebrae such that the spacing and angular orientation between implant holders associated with a particular vertebra can be readily adjusted and maintained by engagement with the respective transverse bridge. The inter-level linking assemblies can be releasably coupled to connecting members of the transverse bridges, for example, such that the spacing and angular orientation between the linked derotation instrument assemblies can be readily adjusted and maintained with clamping and connector assemblies that secure the derotation instrument assemblies to an elongate link member extending between the derotation instrument assemblies.

The inter-level linking assemblies can interconnect the derotation instrument assemblies in a rigid fashion so that the engagement relationship between the components is maintained during derotation of the spinal column. It is further contemplated that at least limited slippage or movement between the inter-level linking assemblies and the derotation instrument assemblies can be provided as the spinal column is straightened to accommodate non-uniform relative displacement among the corrected vertebrae that may be required.

In FIG. 1 there is shown one embodiment of a derotation instrument assembly 500 coupled to implants 550. Implants 550 are engaged to a vertebral body V1. In one specific application, implants 550 are bone anchors secured to respective ones of the pedicles of vertebral body V1. Implants 550 each include a receiver portion 552 for receiving a respective elongated spinal stabilization element 554 positionable along the spinal column and securable to the implants to maintain a positioning of one or more vertebral bodies. In the illustrated embodiment, the implants are bone screws with a U-shaped head portion providing a receiver to receive a spinal rod. Other embodiments contemplate saddles, posts, clamping members, side-loading receivers or other receiver type members extending from a bone engaging portion in the form of a staple, hook, screw, interbody device, intrabody device or other bone engaging member.

Derotation instrument assembly 500 includes implant holders 502 removably engaged to respective ones of the implants 550 and extending proximally therefrom. The implant holders 502 can be interconnected with one another in a bilateral fashion with a transverse bridge 504 extending therebetween. Each of the implant holders 502 further includes a derotation handle 506 extending proximally from the location along the implant holder 502 to which transverse bridge 504 is engaged. Derotation handles 506 extend in a direction that is generally parallel to and/or forms an axial extension of the clamp portion of the respective implant holder 502, and thus extends in a direction that is generally parallel to the sagittal plane of the spinal column when implants 550 are engaged to the pedicles.

Derotation instrument assembly 500 can be manipulated with one or both of derotation handles 506 to displace, pull, twist or align the vertebra to which implants 550 is engaged into the desired alignment with the spinal column. Accordingly, manipulation of multiple anchors engaged to the spinal column can be completed with a single-handle, although the application of such forces through multiple handles is not precluded. The interconnection of the implants 550 results in the corrective forces being distributed to both implants and thus to multiple locations on the vertebral body. This can reduce stress concentrations at any single bone/implant interface as the manipulation forces are applied.

Figure 2:
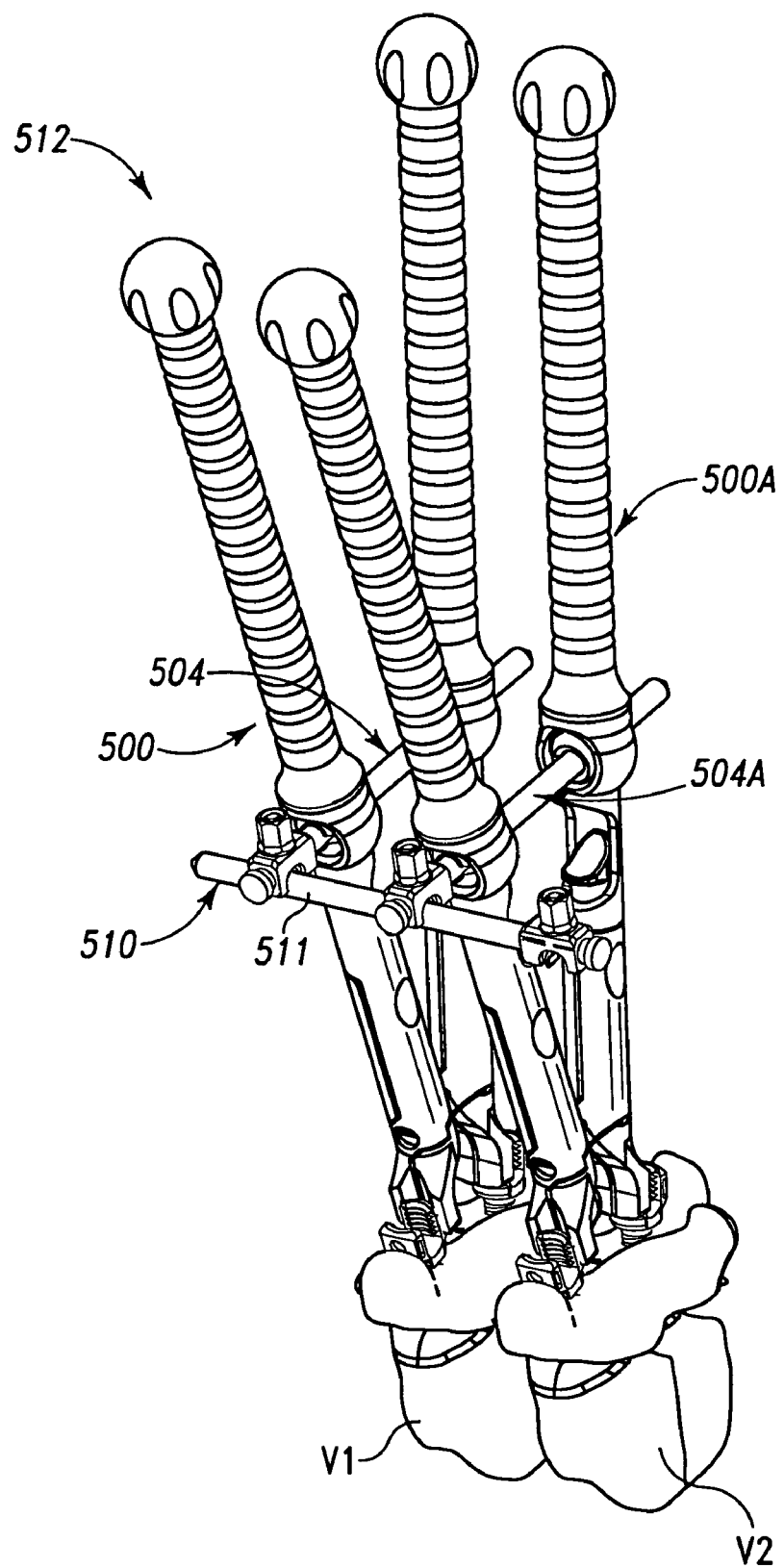
FIG. 2 is a perspective view of a derotation system for multiple vertebral levels.

It is further contemplated that a number of derotation instrument assemblies 500 can be coupled to one another by one or more inter-level linking assemblies 510 with a link member 511 extending between and coupled to, for example, transverse bridges 504 and 504A of the respective derotation instrument assemblies 500 and 500A shown in FIG. 2. The inter-level, linked instrument assemblies 500, 500A provide a derotation system 512 that facilitates the application of and distribution of derotation, correction, alignment and other forces to various bony structures engaged by the bone implants and interconnected within the system, such as first and second vertebra V1 and V2. Accordingly, the resultant stress on any one of the implants and the bone to which the implant is engaged is distributed to multiple locations and/or multiple vertebrae.

Figure 3:
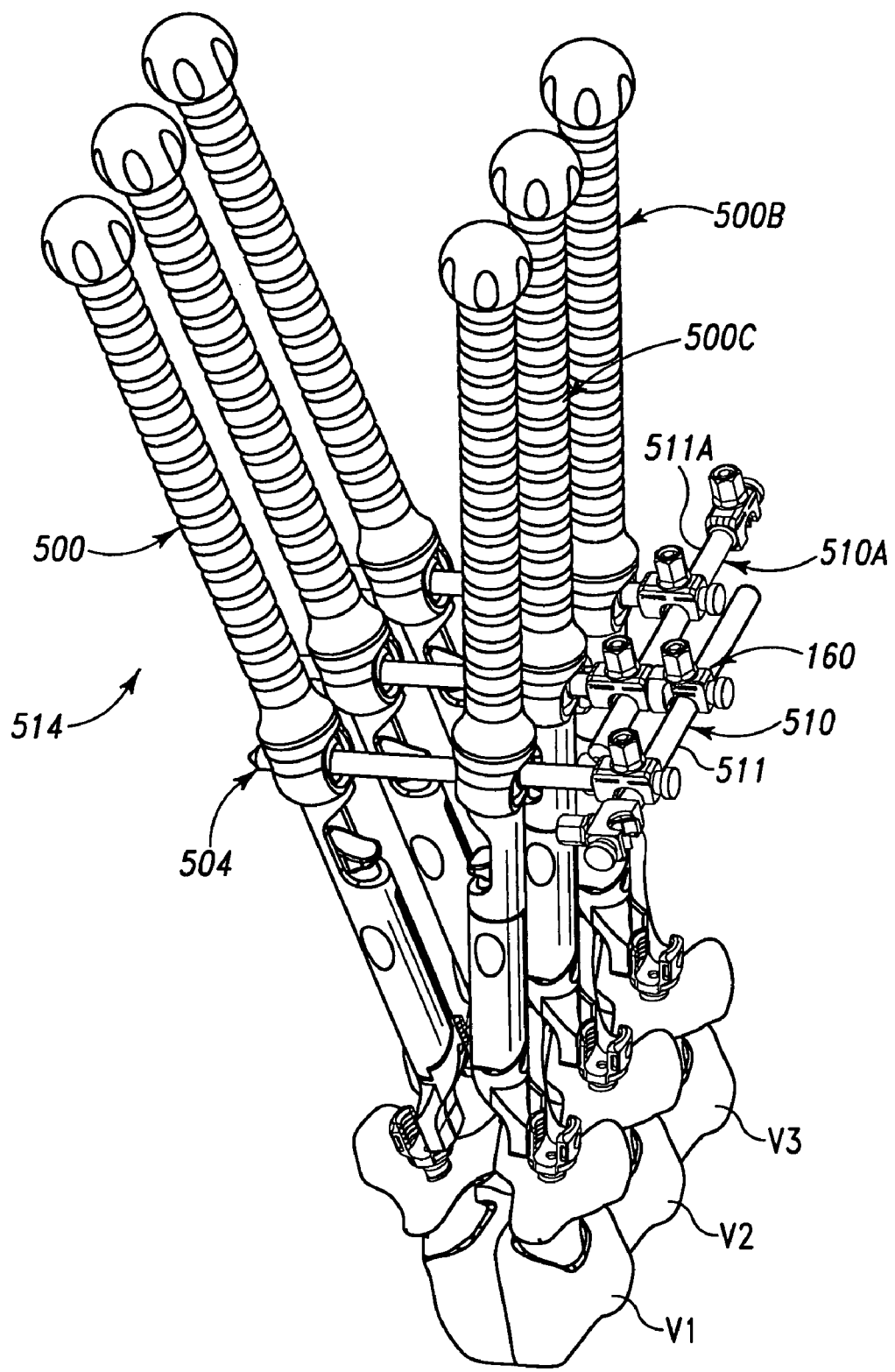
FIG. 3 is a perspective view of another derotation system for multiple levels.

It is contemplated that any one, two or three or more vertebral levels with derotation instrument assemblies 500 can be linked. It is further contemplated that any subset of instrumented vertebral levels in a system could be linked. For example, FIG. 3 shows a derotation system 514 for three vertebrae V1, V2 and V3. Derotation instrument assemblies 500 and 500A are linked by inter-level linking assembly 510, and derotation instrument assemblies 500A and 500B are linked by a second inter-level linking assembly 510A with a second linking member 511A.

Figure 4:
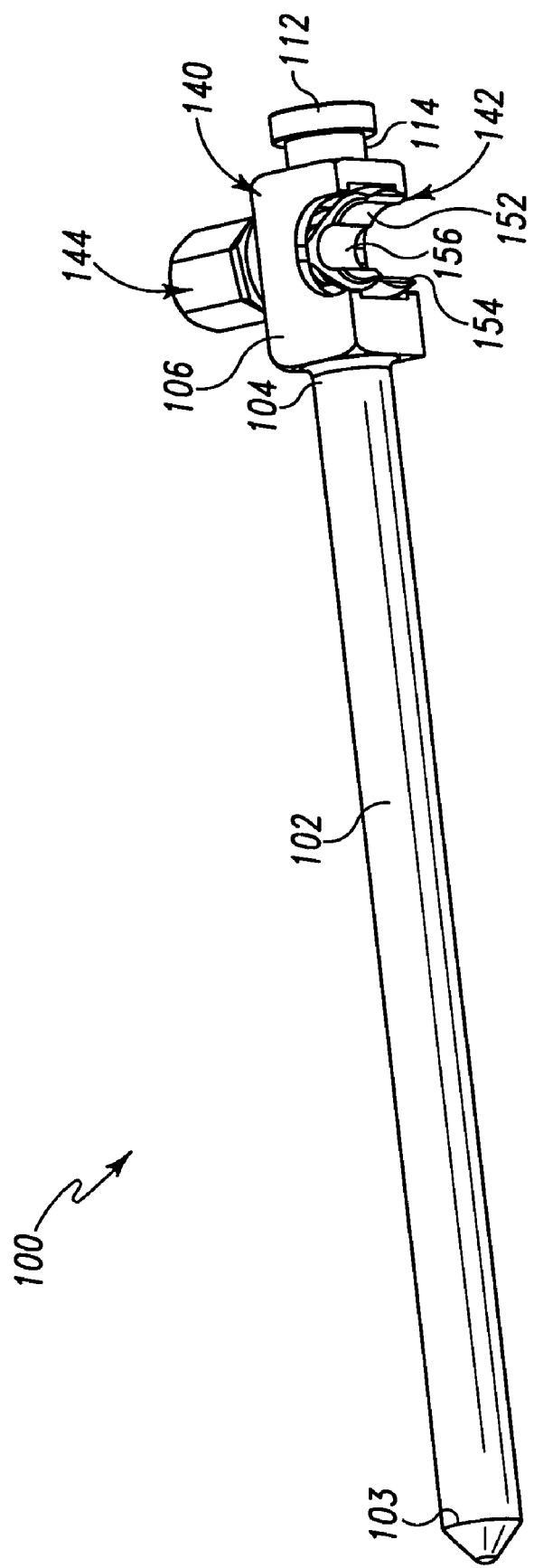
FIG. 4 is a perspective view of a transverse bridge.
Figure 5:
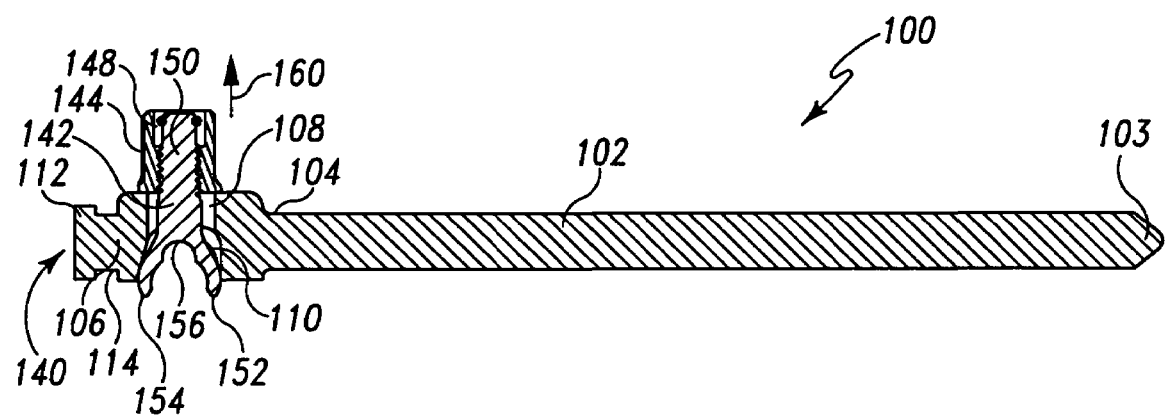
FIG. 5 is a longitudinal sectional view of the transverse bridge of FIG. 4.

Referring now to FIGS. 4-5, one specific example of a transverse bridge 504 is shown in the form of transverse bridge 100. Transverse bridge 100 includes a transverse connecting member 102 and a clamping assembly 140 positioned at one end of connecting member 102. Clamping assembly 140 can be removably engaged to connecting member 102 or formed as an integral unitary component therewith.

Transverse connecting member 102 can have a circular shaped cross-section as shown in section view in FIG. 4. Other cross-sectional shapes are also contemplated, including diamond, square, rectangular, polygonal, and non-circular shapes, for example. Connecting member 102 extends between a first end 103 and a second end 104. First end 103 can be tapered as shown to facilitate placement of connecting member 102 through an implant holder, as shown in FIGS. 1-3. A non-tapered first end 103 is also contemplated. Second end 104 can include clamping assembly 140 either removably or non-removably attached thereto.

Clamping assembly 140 includes a clamping portion 142 and a securing portion 144 that is operable to secure and release clamping portion 142 to transverse connecting member 102. Connecting member 102 includes a mounting member 106 adjacent second end 104, and a bore 108 extending through mounting member 106 through which clamping portion 142 extends. Securing portion 144 further includes a bore 148 for receiving a proximal post 150 of clamping portion 142. Securing portion 144 can include internal threads in bore 148 to threadingly engage post 150.

Clamping portion 142 further includes clamping arms 152, 154 at an end of post 150 and a hinge portion 156 between arms 152, 154. Arms 152, 154 are positioned in recess 110 of mounting member 106 on a side opposite of securing portion 144. Securing portion 144 is rotatable to threadingly displace clamping portion 142 relative thereto. For example, securing portion 144 can be rotated to displace clamping portion 142 in the direction of arrow 160, as shown in FIG. 5. This in turn presses arms 152, 154 against mounting member 106 and moves arms 152, 154 toward one another into engagement with a linking member or other element positioned therebetween, as shown in FIGS. 2 and 3.

Figure 6:
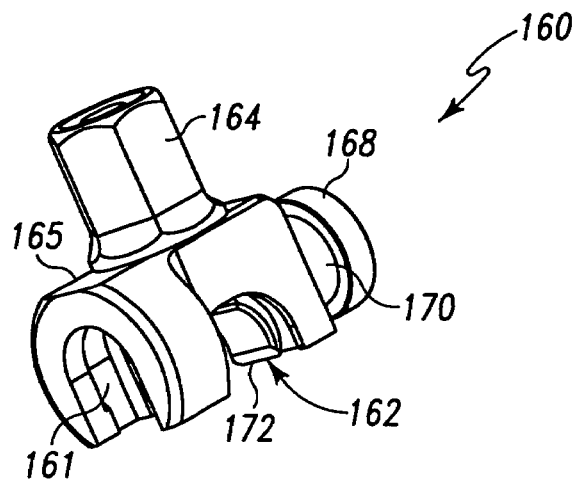
FIG. 6 is a perspective view of a connector assembly.
Figure 9:
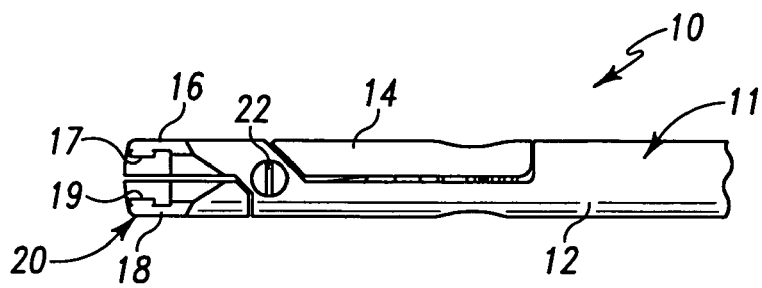
FIG. 9 is an elevation view of a clamp portion of the implant holder of FIG. 7 in a closed position.

Mounting member 106 further includes an end flange 112 forming an end of connecting member 102 and a groove 114 adjacent to end flange 112. End flange 112 can receive a connector assembly 160, such as shown in FIG. 6. Connector assembly 160 can be similar to clamping assembly 140 discussed above, but is configured without a connecting member. In contrast, connector assembly 160 includes an end opening defining a receiving slot 161 adjacent one end thereof to receive, for example, end flange 112 of connecting member 102. This allows a connecting member 102 to be extended with one or more additional connector assemblies 160, such as shown in FIG. 3, to receive a linking member of another inter-level linking assembly.

Connector assembly 160 can be provided with a clamping portion 162 and a securing portion 164 mounted to a body 165. The securing portion 164 is operable to move the clamping portion into contact with body 165 and close arms 172 (only one shown in FIG. 6) of clamping portion 162 about, for example, the link member 514 of an inter-level linking assembly 510. Body 165 can further include an end flange 168 and a groove 170 adjacent thereto to receive another connector assembly 160 in end-to-end relation.

Referring now to FIG. 7, one specific example of implant holder 502 will be discussed with respect to an implant holder 10. Implant holder 10 includes a clamp portion 11 and a handle portion 30 extending axially and proximally from clamp portion 11. A joint 80 is provided between clamp portion 11 and handle portion 30 for engaging transverse bridge 504.

Joint 80 can be formed by an end member 82 at the proximal end of clamp portion 11. End member 82 defines a proximally opening receptacle that houses a ball member 84. Ball member 84 includes a passage 86 extending therethrough to receive, for example, connecting member 102 of transverse bridge 100. Ball member 84 is rotatable so that the angular orientation between implant holder 10 and connecting member 102 can be easily adjusted and accommodated. Ball member 84 further includes relief 88 that allows the ball member to flex and securely engage the connecting member 102 in passage 86 when compressed.

Handle portion 30 extends proximally from joint 80, and can include a distal end 32 threadingly engaged to end member 82 to capture ball member 84 in the receptacle. Handle portion 30 further includes an elongated shaft portion 34 defining an internal passage 36 extending axially therethrough. Internal threads 38 are provided adjacent the distal end of passage 36.

In FIG. 8 there is shown a locking member 90 that is positionable through passage 36 and into engagement with ball member 84. Locking member 90 includes an elongated shaft 92 extending proximally from a distal engaging end 93. Engaging end 93 can include a threaded portion 94 to threadingly engage internal threads 38 of handle portion 30. Engaging end 93 further includes an end wall 95 that can be concave, inwardly curved or otherwise shaped to engage ball member 84 when shaft 92 is positioned in internal passage 36 of handle portion 30.

A knob member 96 is provided at the proximal end of shaft 92. Knob member 96 defines an axially extending and distally opening receptacle 97 about shaft 92. The proximal end 35 of shaft portion 34 of handle portion 30 can be received in receptacle 97 as locking member is distally, threadingly advanced into handle portion 30. In particular, the length of shaft 92 is sized so that knob member 92 resides proximally of the proximal end 35 of handle portion 30 when threaded portion 94 is threadingly engaged to internal threads 38. Knob member 92 can be grasped by the user to rotate locking member 90 and threadingly advance engaging end 93 into contact with ball member 84. As locking member 90 presses against ball member 84, ball member 84 compresses about relief 88 and into firm engagement with the connecting member 102 in passage 86.

Figure 10:
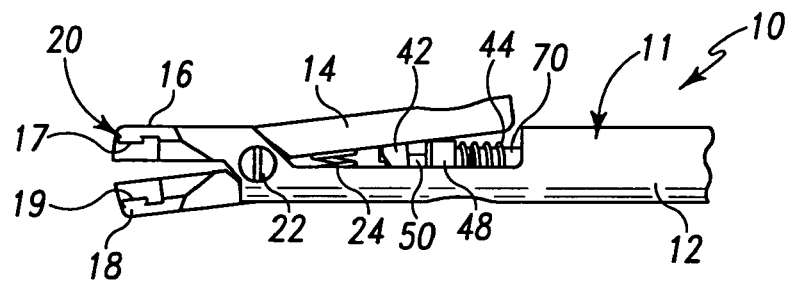
FIG. 10 is an elevation view of the clamp portion of FIG. 9 in an open position.

Referring now to FIGS. 9-17, clamp portion 11 of implant holder 10 will be further discussed. Clamp portion 11 includes a first arm 12 in the form of a tubular body and a second arm 14 providing a clamping arm that is pivotally coupled to first arm 12. Each of the first and second arms 12, 14 includes a respective distal end portion 16, 18 of a distal holding end 20 of implant holder 10. Each of the portions 16, 18 forms a space in which to receive a portion of the bone implant, and further includes a projection 17, 19 extending into the space toward the other portion 16, 18. The projections 17, 19 are received in detents formed in the receiver of the implant to which holder 10 is engaged by clamping arms 12, 14 to the receiver of the implant when implant holder 10 is closed, as shown FIG. 9 for example. To release the implant, implant holder 10 is opened by pivoting second arm 14 about pivotal connection 22 with first arm 12, as shown in FIG. 10.

Figure 11:
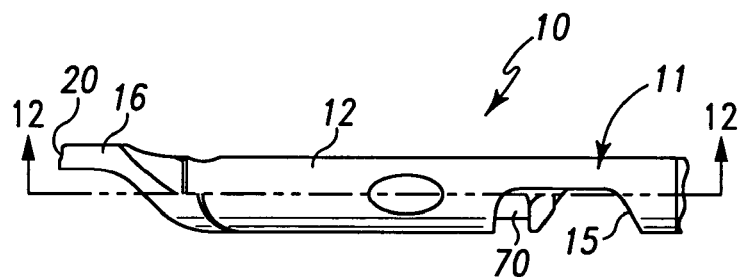
FIG. 11 is an elevation view of the clamp portion of FIG. 9 rotated 90 degrees about its longitudinal axis.

Arms 12, 14 cross-over one another in a scissors type arrangement, and include inter-fitting recessed portions 30, 32, respectively, at connection 22 so that end portions 16, 18 are aligned with one another. Furthermore, as shown in FIG. 11, arms 12, 14 include a slight bend so that end portions 16, 18 are offset to one side of the longitudinal axis 13 of implant holder 10. Arms 12, 14 are movable relative to one another about connection 22 in a first plane that includes longitudinal axis 13. Distal portions 16, 18 are movable in a relative to one another by pivoting arms 12, 14, and move in a second plane that is generally parallel to the plane including longitudinal axis 13. In addition, the space between end portions 16, 18 opens away from axis 13 to so that the implant to which implant holder 10 is engaged can remain substantially unobstructed for engagement with another implant or system component.

Arms 12, 14 are spring biased toward the open position with a spring 24 positioned in wells 26, 28 formed by respective ones of the arms 12, 14. Wells 26, 28 are oriented toward one another, and located proximally of the pivotal connection 22 between arms 12, 14. In order to secure arms 12, 14 in the closed position in engagement with the implant, a latching mechanism 40 is provided between arms 12, 14.

Latching mechanism 40 includes a latch member 42 extending from second arm 14 and a holding member 50 mounted to first arm 12 that is releasably engageable by latch member 42. Latching mechanism 40 also includes a release button 70 coupled to and extending proximally from holding member 50 between arms 12, 14, and a spring 44 biasing holding member 50 into engagement with latch member 42 and further biasing release button 70 proximally.

First arm 12 includes a collar 48 extending therefrom into a receptacle defined between arms 12, 14 in which latching mechanism 40 is located Holding member 50 extends through collar 48 and is axially movable therein while collar 48 maintains holding member 50 in axial alignment with the remaining portions of latching mechanism 40. In addition, an alignment pin 46 can be press fit in collar 48 and extend therefrom into a slot 52 (FIG. 16) along a portion of the length of holding member 50 to maintain holding member 50 in rotational alignment with latching mechanism 40. Other embodiments contemplate that collar 48 and/or alignment pin 46 can be eliminated.

Figure 12:
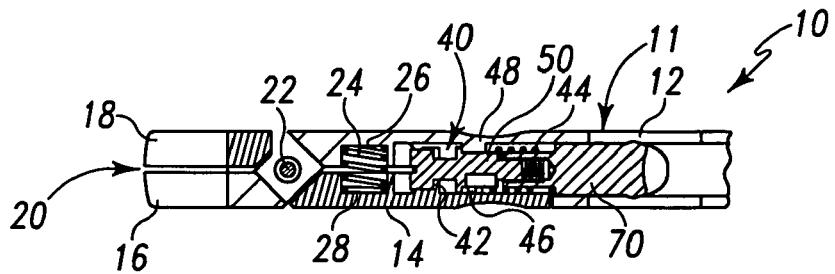
FIG. 12 is a section view along line 12-12 of FIG. 11.
Figure 15:
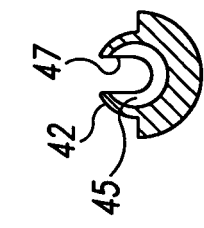
FIG. 15 is a sectional view looking proximally at a latch member of the implant holder of FIG. 7.
Figure 15:
Figure 16:
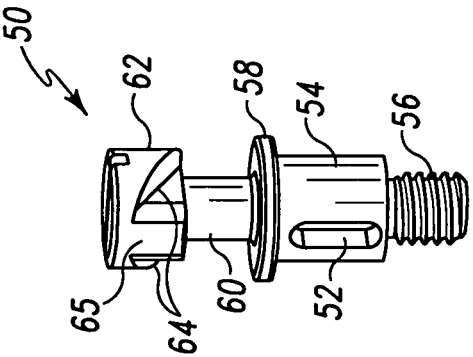
FIG. 16 is a perspective view of a holding member of the implant holder of FIG. 7.
Figure 13:
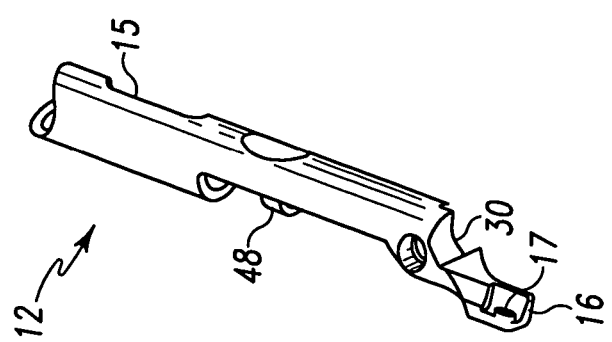
FIG. 13 is a perspective view of a first arm of the implant holder of FIG. 7.

Holding member 50 is shown further in FIG. 16. Holding member 50 includes a central body 54 defining axial slot 52 therealong. A connector portion 56 extends from a proximal end of central body 54, and is threadingly received in a distal end opening of release button 70, as shown in FIG. 12. The distal end of central body 54 includes a radially outwardly extending flange 58 that abuttingly engages collar 48 to limit the proximal displacement of release button 70 and holding member 50 under the bias of spring 44.

Figure 14:
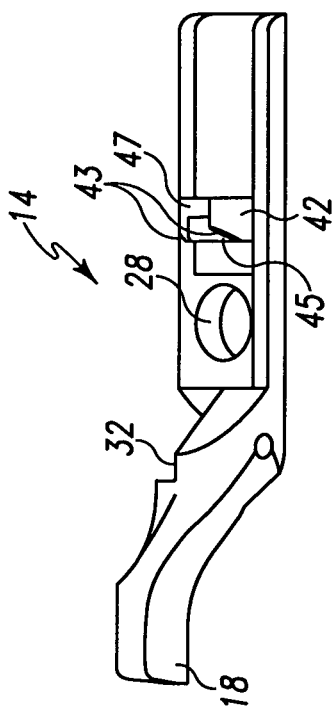
FIG. 14 is a perspective view of a second arm of the implant holder of FIG. 7.

Holding member 50 also includes a stem 60 extending distally from flange 58 to a latch receiving member 62. Latch receiving member 62 includes a cylindrical body with inclined notched areas 64 and a central projection area 65 between inclined notched areas 64. In the open position, latch member 42 includes sloped portions 43 that reside along inclined notches areas 64, as shown in FIG. 14. When closing arms 12, 14 to engage the implant between portions 16, 18, the sloped portions 43 slide along the respective adjacent inclined notched areas 64 to distally and axially displace holding member 50 until the receptacle 45 (FIG. 15) of latch member 42 aligns with and receives the cylindrical body of latch receiving member 62, as shown in FIG. 12. In the closed position, arm 14 is prevented from pivoting away from arm 12 by engagement of latch member 42 around receiving member 62 of holding member 50. To release latch mechanism 40 and allow arm 14 to pivot away from arm 12, release button 70 is depressed to displace holding member 50 distally sufficiently to align stem 60 with slotted opening 47 (FIG. 15) of latch member 42. This allows receptacle 45 to become disengaged or displaced from about latch receiving member 62, and spring 44 pushes arm 14 away from arm 12 and rotates arm 14 about connection 22 to the open position of FIG. 10.

Figure 17:
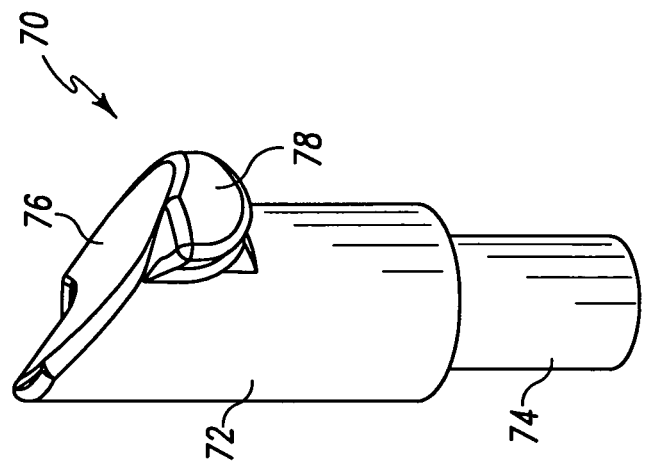
FIG. 17 is a perspective view of a release button of the implant holder of FIG. 7.

Release button 70 is further shown in FIG. 17, and includes a body portion 72 extending between a distal end member 74 and a proximal end 76. Distal end member 74 defines the opening which receives connector portion 56 of holding member 50. Proximal end 76 includes a concavely curved surface to facilitate application of manual depression forces with a thumb or finger to proximally displace button 70 and thus latch mechanism 40 between arms 12, 14. Button 70 is accessible through a notched area 13 of first arm 12, as shown in FIG. 11. An outwardly extending lip 78 adjacent proximal end 76 can contact first arm 12 in notched area 15 to maintain alignment of release button 70 as it is moved therein and to limit distal displacement of button 70.

Figure 18:
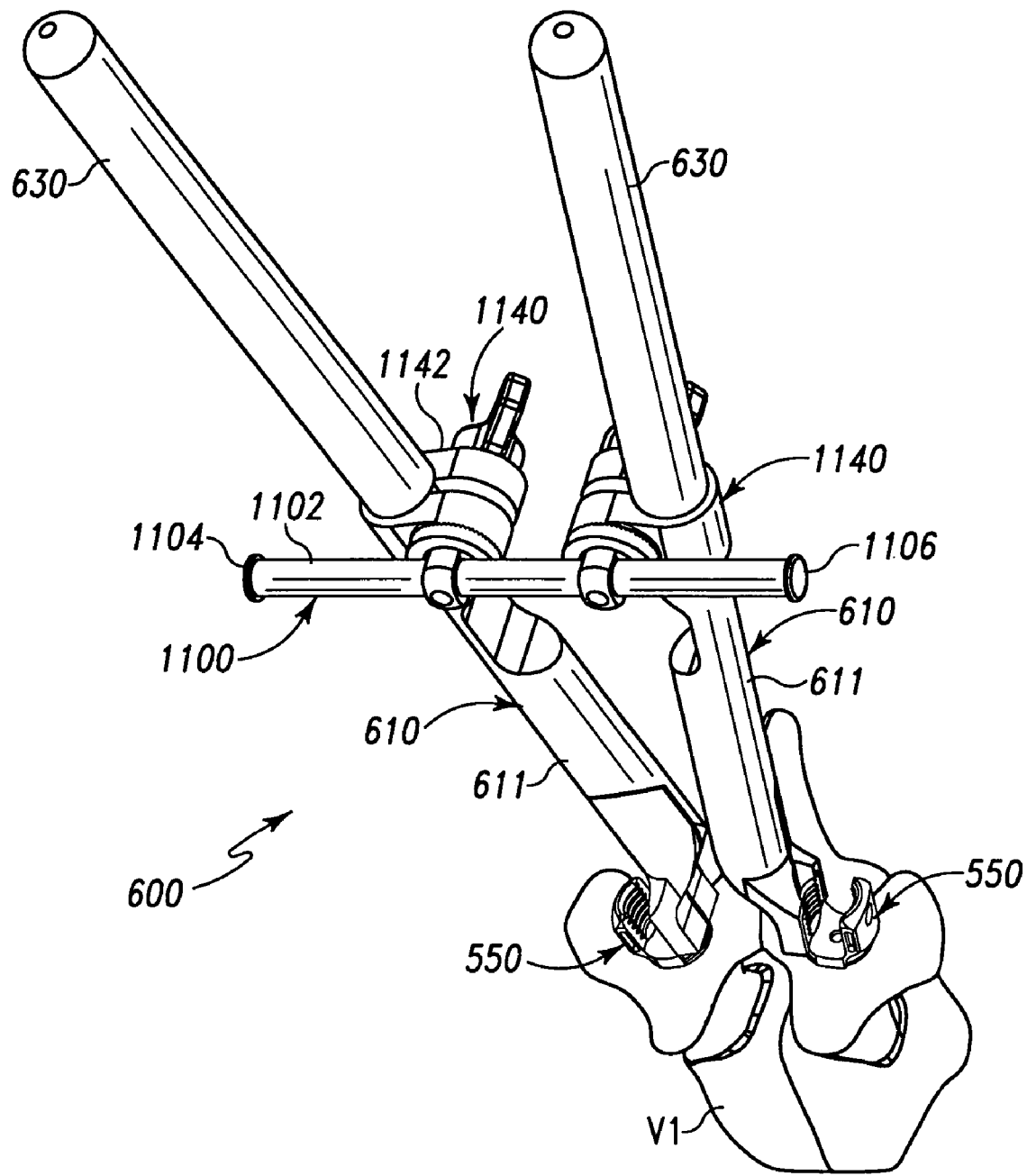
FIG. 18 is a perspective of another embodiment derotation instrument assembly engaged to a vertebra.
Figure 19:
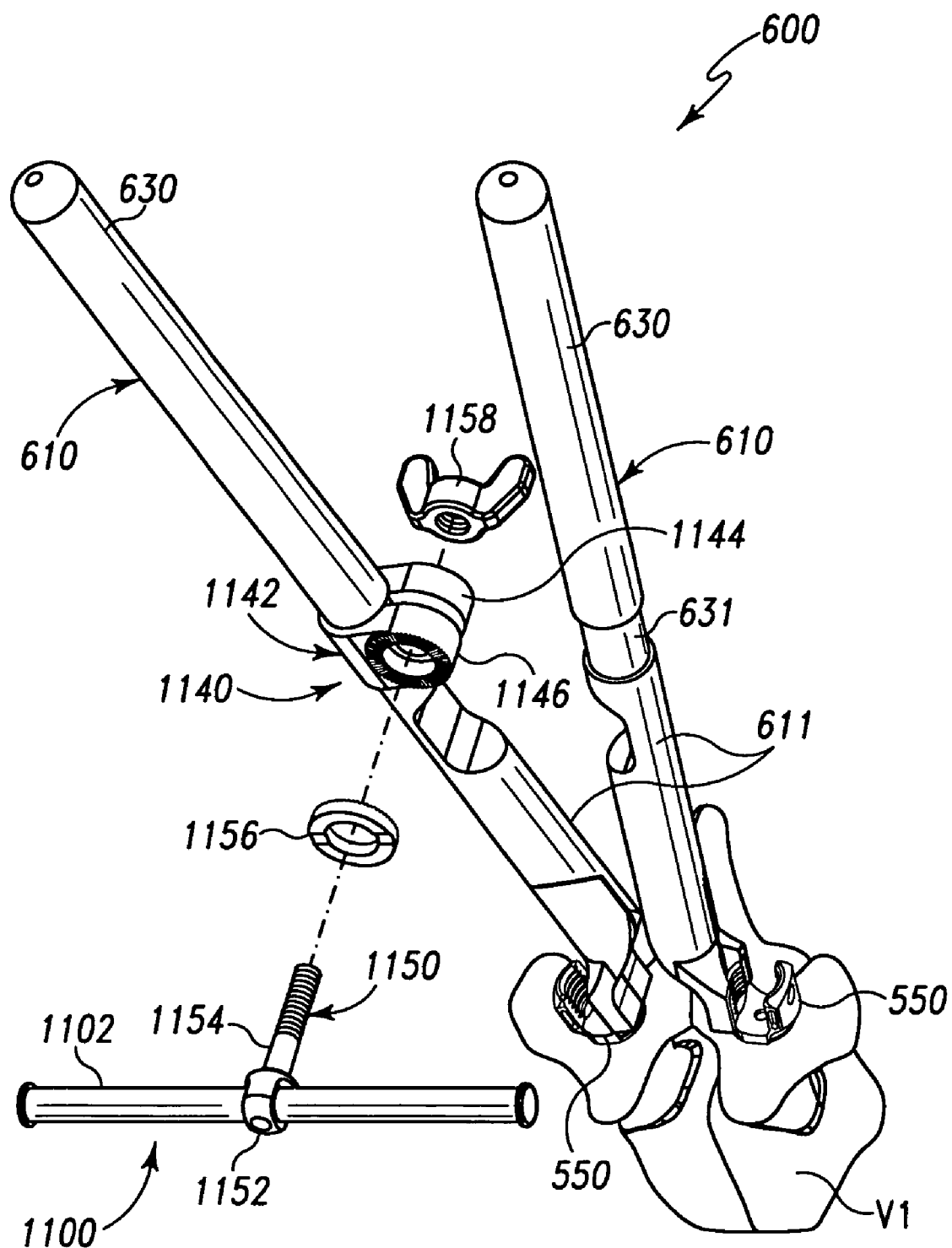
FIG. 19 is a partially exploded perspective view of a portion of the derotation instrument assembly of FIG. 18.

Other embodiment transverse bridge, implant holder and derotation instrument assemblies and systems are also contemplated. For example, FIGS. 18 and 19 show a derotation instrument assembly 600 engaged to implants 550 that are engaged to respective pedicles of vertebra V1. Derotation instrument assembly 600 includes implant holders 610 each having a distal clamp portion 611 releasably engageable to respective ones of the implants 550 and a proximal handle portion 630. A transverse bridge 1100 extends between and is engaged to implant holders 610 at a joint 631 located between handle portion 630 and clamp portion 611 of each of the implant holders 610.

Transverse bridge 1100 includes an elongated transverse connecting member 1102 in the form of a connecting rod with end flanges 1104, 1106 at opposite ends thereof. Transverse bridge 1100 further includes clamping assemblies 1140 at or adjacent to the ends of connecting member 1102 that are movable along connecting member 1102 to allow adjustment in the spacing between the implant holders 610. Clamping assemblies 1140 each include a clamping portion 1142 that includes a split-ring type clamping member that is positioned around implant holder 610 at joint 631, and further includes arms 1144, 1146 that are moveable to selectively release and securely engage clamping assembly 1140 at joint 631 of implant holder 610.

Clamping assembly 1140 further includes a securing portion 1150 having a first end 1152 having a ring-shape defining a receptacle for receiving connecting member 1102 therethrough and a mounting portion 1154 in the form of a post extending from first end 1152. Arms 1144, 1146 define a bore through which mounting portion 1154 extends. A seating washer 1156 is positioned about mounting portion 1154 between first end 1152 and arm 1146, and a locking member 1158 is positioned about mounting portion 1154 adjacent arm 1144. Locking member 1158 can be in the form of a wing nut threadingly engaged to the post-like structure of mounting portion 1154, although other engagement relationships and forms for locking member 1158 are contemplated. As locking member 1158 is advanced along mounting portion 1154, first end 1152 of securing portion 1150 is drawn toward locking member 1158, and connecting member 1102 seats against seating washer 1156, and arms 1144, 1146 are compressed between washer 1156 and locking member 1158 to tightly grip joint 631 of the respective implant holder 610. Connecting member 1102 is clamped between seating washer 1156 and first end 1152 to lock clamping assembly 1140 in position along connecting member 1102.

Figure 20:
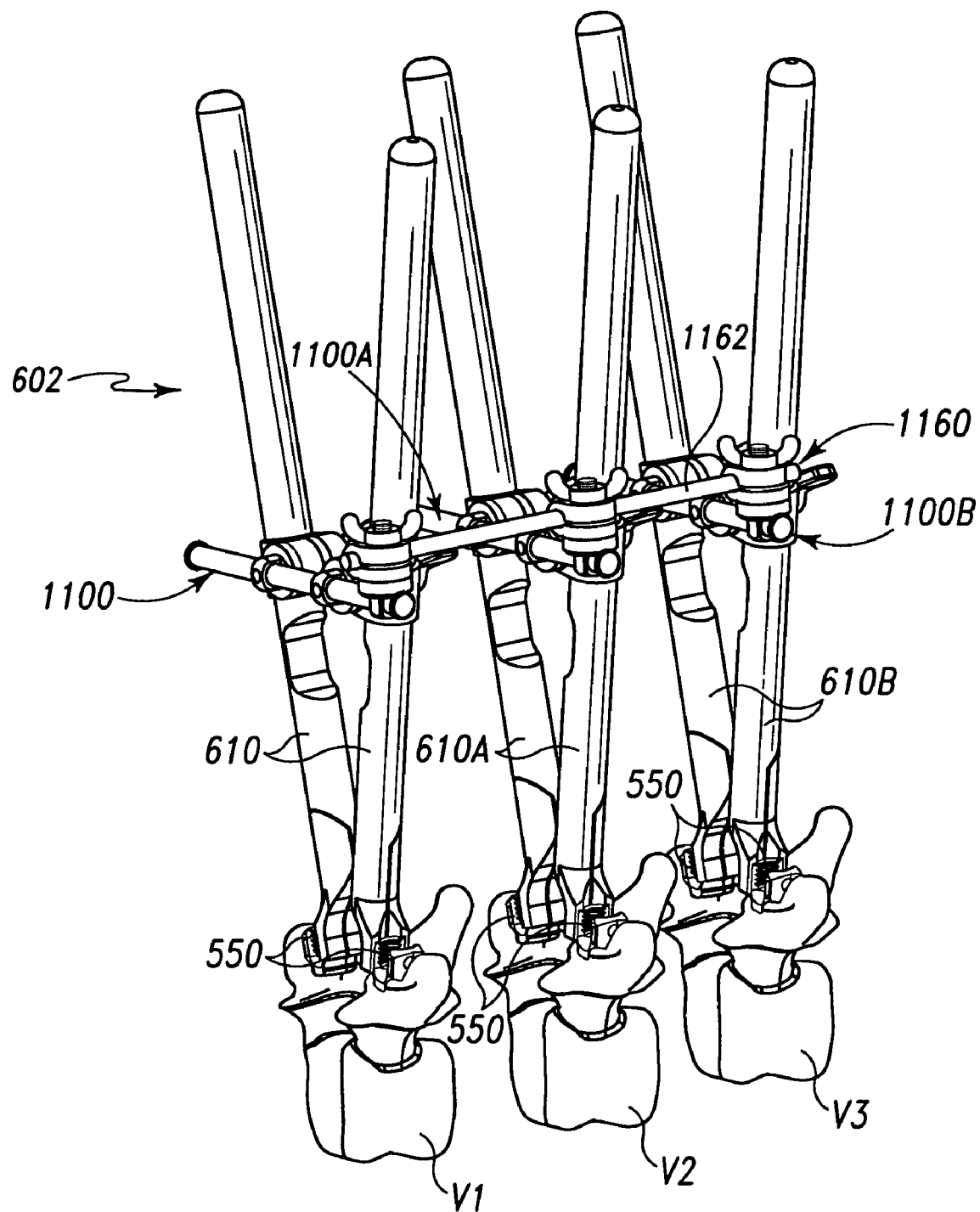
FIG. 20 is a perspective view of a derotation system employing a number of derotation instrument assemblies of FIG. 18 along inter-linked vertebral levels.

Derotation instrument assembly 600 can be engaged to multiple vertebrae V1, V2, V3 with an inter-level linking assembly 1160, as shown in FIG. 20, for example. Linking assembly 1160 includes an elongated link member 1162 that extends between and is engaged to the connecting members of each of the transverse bridges 1100, 1100A and 1100B. In the illustrated embodiment, linking assembly 1160 include clamp assemblies like clamp assembly 1140 discussed above that extend between and engage linking member 1162 and to the connecting member of the transverse bridges to provide a derotation system 602, such as shown FIG. 20.

Figure 21:
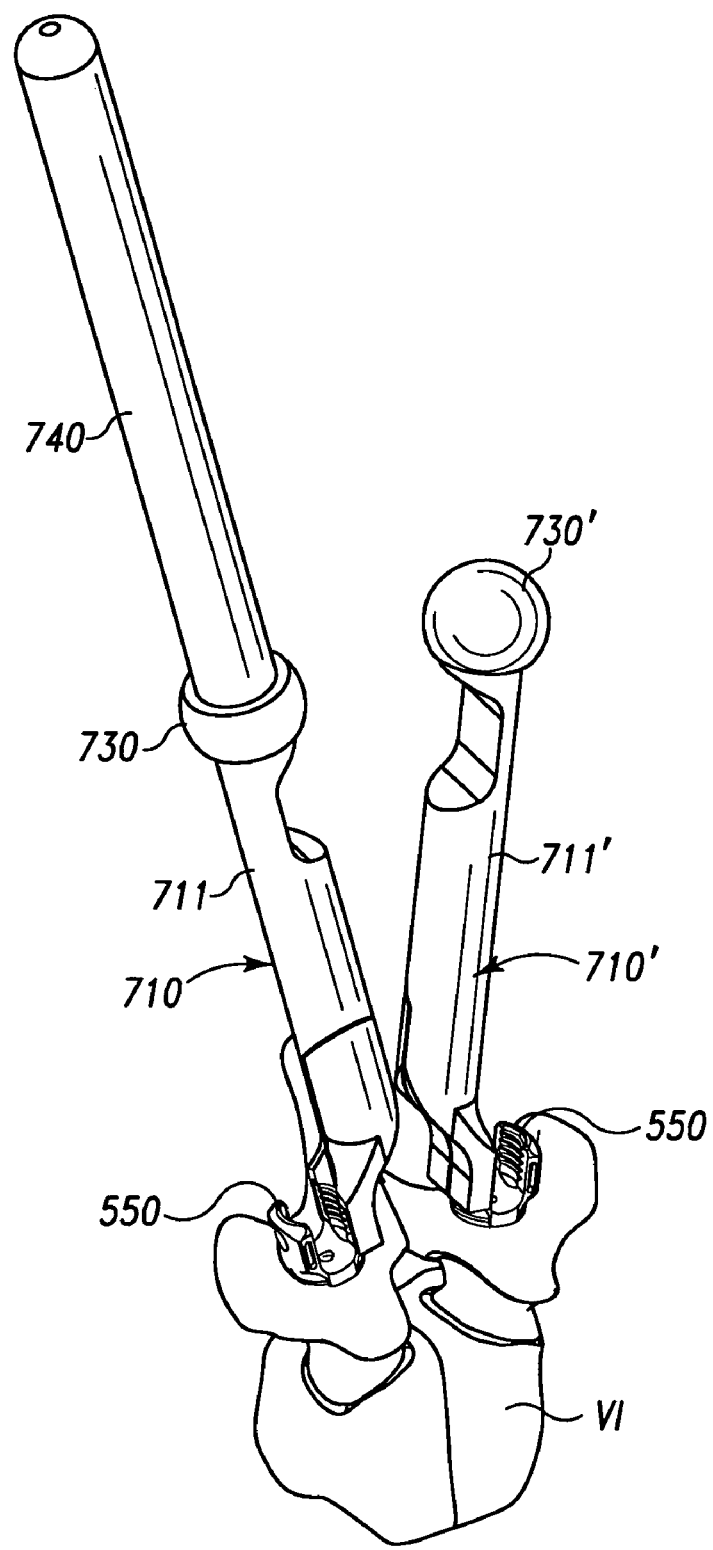
FIG. 21 is a perspective view of another embodiment implant holders engaged to implants on respective sides of a vertebral body.

Referring now to FIG. 21, there is shown another embodiment implant holder 710 engaged to one of the implants 550 and a further embodiment implant holder 710' engaged to another of the implants 550. Implant holder 710' includes a distal clamp portion 711' that can be configured similarly to clamp portion 11 of implant holder 10 discussed above. However, implant holder 710' includes a joint 730' at the proximal end of clamp portion 711' and does not include a handle or other structure extending proximally from joint 730'. Implant holder 710, on the other hand, includes a joint 730 at the proximal end of clamp portion 711 and a handle portion 740 extending proximally from joint 730. In both embodiments, joint 730, 730' is configured as a ball-like member or a portion with an outer spherically shaped surface.

Figure 22:
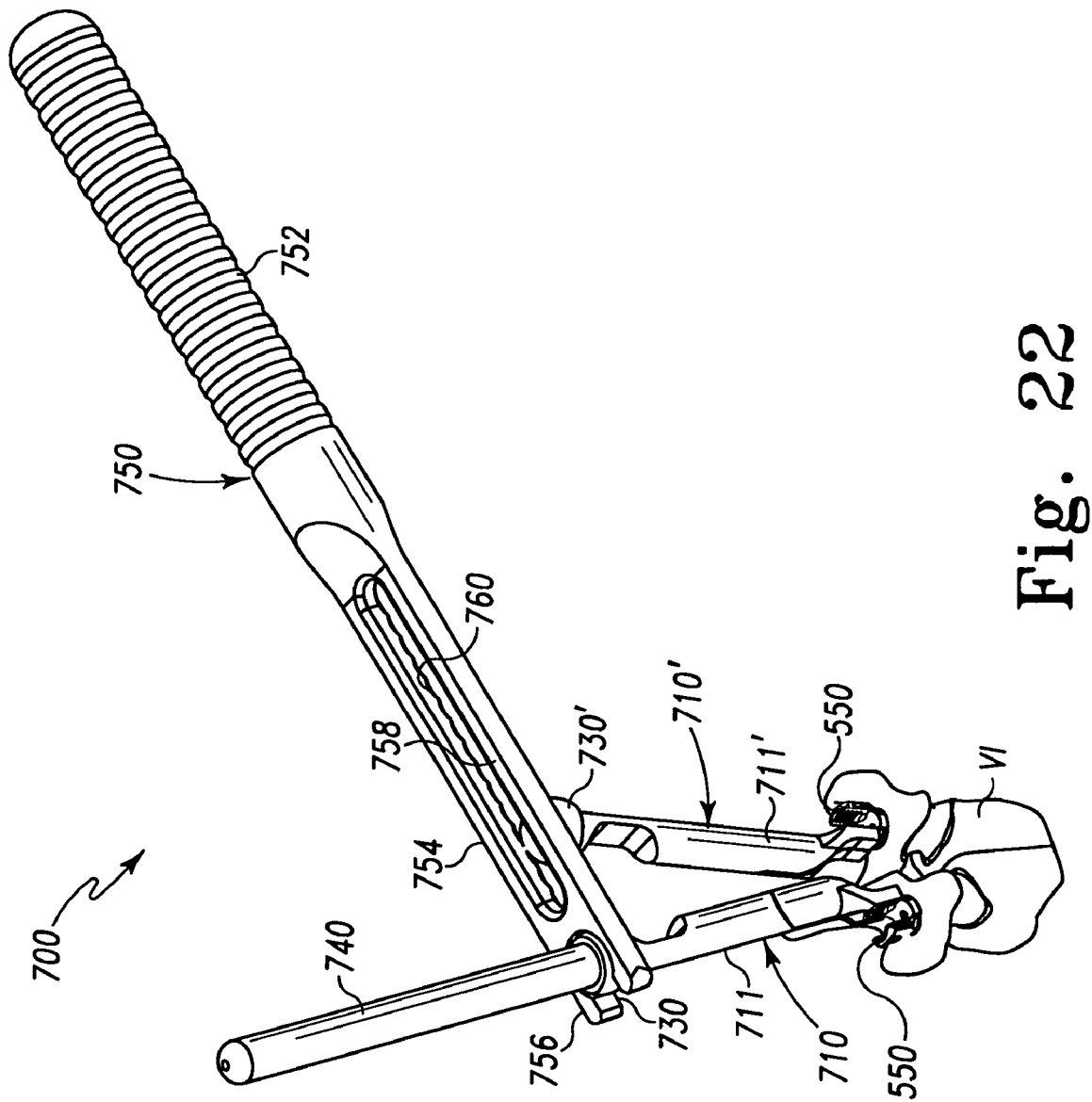
FIG. 22 is a perspective view of a transverse bridge being engaged between the implant holders of FIG. 21.

In FIG. 22 there is shown a transverse bridge 750. Transverse bridge 750 includes a handle portion 752 at one end thereof, and a connecting member 754 extending from handle portion 752. An end portion 756 of connecting member 754 includes a fork-like shape to receive joint 730 of implant holder 710 therein in pivoting relation. A slotted portion 758 extends between end portion 756 and handle portion 752. Slotted portion 758 defines a central slot 760 with a number of scallops or partially-spherical receiving areas to receive joint 730' therein at any one of the number of locations along the slotted portion 1158.

The partially spherical interface between connecting member 754 and the implant holders 710, 710' allows engagement in any one of a number of angular orientations therebetween. The transverse bridge 750 couples implant holders 710, 710' to one another to provide a derotation instrument assembly 700 that distributes derotation forces applied with handle portion 730 to each of the implants 550. Furthermore, handle portion 752 of transverse bridge 750 provides a handle that is transversely oriented to the implant holders 710, 710' and when implants 550 are engaged to the pedicles to the sagittal plane of the spinal column. Accordingly, derotation forces and other maneuvers applied through handle portion 752 can likewise be distributed to each of the implants 550.

Figure 23:
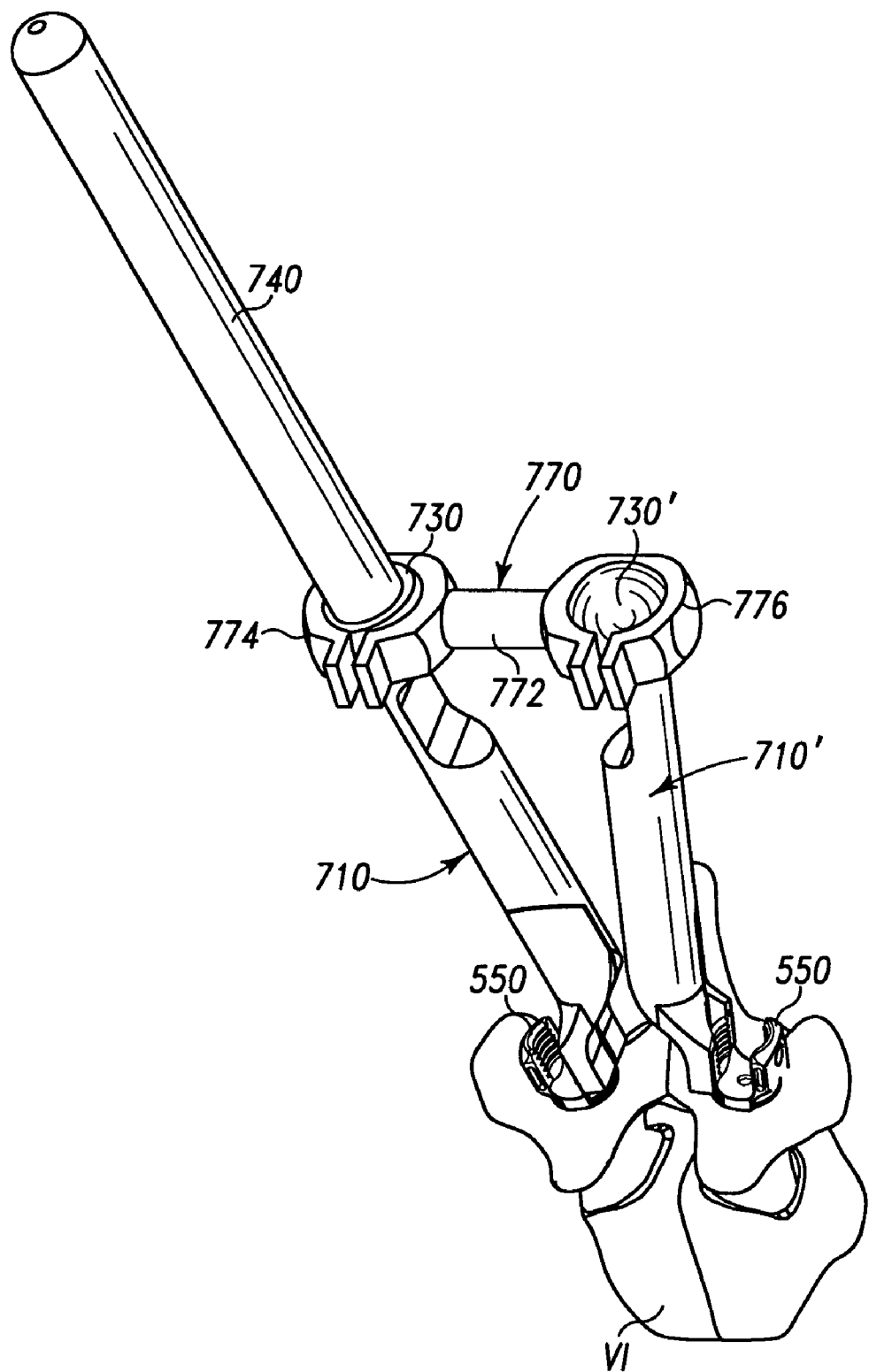
FIG. 23 shows another embodiment transverse bridge engaged between the implant holders of FIG. 21.

FIG. 23 shows another embodiment transverse bridge 770 extending between and engaged to implant holders 710, 710'. Transverse bridge 770 includes an elongated connecting member 772 and clamping members 774, 776 at opposite ends of connecting member 772. Clamping members 774, 776 can form a split-ring type arrangement with free ends that can move relative to one another to fit around and clampingly engage the respective joints 730, 730' of implant holders 710, 710'. The free ends of the clamping members can be engaged toward one another to securely clamp the clamping members 774, 776 about the respective joint 730, 730'.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for correcting alignment of one or more vertebrae of a spine, comprising:

first and second implants engageable to one of the one or more vertebrae, said first and second implants being configured for engagement with respective ones of first and second stabilization elements positionable along the spine; and a derotation instrument assembly including first and second elongated implant holders releasably engageable to respective ones of said first and second implants, a transverse bridge positionable between and engageable to each of said first and second implant holders at a location spaced proximally from said first and second implants, wherein each of said first and second implant holders includes a derotation handle extending proximally from said location, said derotation handles being associated with said respective implant holders in a manner that permits forces applied to either of said handles to be directed to said transverse bridge, thereby manipulating both said first and second implant holders when engaged to said bridge and both said first and second implants when engaged to said first and second implant holders, wherein said location of at least one of said first and second implant holders includes a first joint, said first joint including a ball member pivotally captured by said handle in a receptacle formed at said location and said transverse bridge includes an elongated connecting member positioned through a passage formed by said ball member, wherein said at least one of said first and second implant holders includes a first arm extending distally from said first joint to a second joint and a second arm pivotally coupled to said first arm at said second joint, wherein said second arm extends proximally from said second joint to a proximal end located between said first and second joints and said second arm extends distally from said second joint to a distal end, said proximal end of said second arm pivotable about said second joint toward said first arm to move said distal end of said second arm toward a distal end of said first arm to engage said respective one of said first and second implants between said first and second arms.

2. The system of claim 1, wherein said implant holders each include a distal clamp portion formed by said first and second arms distal of said second joint.

3. The system of claim 2, wherein said joint includes a partially spherical shape.

4. The system of claim 2, wherein said receptacle is formed adjacent said proximal end of said first arm of said at least one of said first and second implant holders.

5. The system of claim 4, wherein said handle of said at least one of said first and second implant holders includes a locking member, said locking member including an elongated shaft positioned in an elongated axial passage of said handle, said locking member including a distal engaging end in said passage and movable between a first position wherein said ball member is pivotal in said receptacle and a second position wherein said distal engaging end of said locking member engages said ball member in said receptacle and secures it in position therein.

6. The system of claim 5, wherein said ball member includes a relief and said locking member is operable to compress said ball member about said elongate member when engaged to said ball member.

7. The system of claim 5, wherein said handle includes an elongated shaft portion defining said axial passage, said locking member elongated shaft being axially received in said passage in threaded engagement with said shaft portion, said locking member including a proximal knob located proximally of a proximal end of said shaft portion of said handle, said knob defining an axially extending and a distally opening receptacle for receiving said proximal end of said shaft portion.

8. The system of claim 1, further comprising a second derotation instrument assembly including third and fourth elongated implant holders releasably engageable to respective ones of third and fourth implants engageable to a second one of the one or more vertebrae, a second transverse bridge positionable between and engageable to each of said third and fourth implant holders at a location spaced proximally from said third and fourth implants, wherein each of said third and fourth implant holders includes a derotation handle extending proximally from said location, said derotation handles being associated with said respective implant holders in a manner that permits forces applied to either of said handles to be directed to said second transverse bridge, thereby manipulating both said third and fourth implant holders when engaged to said second transverse bridge and both said third and fourth implants when engaged to said third and fourth implant holders.

9. The system of claim 8, further comprising an inter-level linking assembly extending between and engaged to each of said transverse bridges.

10. The system of claim 9, wherein said inter-level linking assembly includes an elongate link member extending between said transverse bridges and said transverse bridges each include an elongate connecting member including a clamping assembly removably engageable to said elongate link member.

11. The system of claim 10, wherein said clamping assemblies each include a clamping portion and a securing portion mounted to said respective connecting member of said transverse bridges, wherein said securing portion is operable to displace said clamping portion relative to said connecting member and move a pair of arms of said clamping portion into contact with said connecting member and relative to one another to clampingly engage said link member between said pair of arms.

12. The system of claim 11, wherein said clamping portion further includes a post extending from said arms through said connecting member, wherein said securing portion threadingly engages said post on a side of said connecting member opposite said pair arms, said securing portion being operable to displace said arms against said connecting member thereby moving said arms toward one another.

13. The system of claim 12, wherein said connecting member includes a mounting portion adjacent one end thereof and said securing portion and clamping portion are mounted to said mounting portion, said connecting member further including a flange extending from said mounting portion and forming an end of said connecting member and further comprising a connector assembly removable engageable to said flange.

14. The system of claim 13, wherein said connector assembly includes:
   a body defining a bore and a recess in one side of said body in communication with said recess;
   a clamping portion including a pair of arms in said recess and a post extending through said bore; and
   a securing portion threadingly engaged with said post and operable to displace said arms against said body in said recess thereby moving said arms toward one another.

15. The system of claim 1, wherein said implant holders each include a distal clamp portion extending along a central longitudinal axis and said clamp portion includes a first arm and a second arm pivotally coupled to said first arm and movable relative to one another in a first plane including said longitudinal axis, said first and second arms each including a distal clamping portion offset to a side of said longitudinal axis and said distal clamping portions move relative to one another in a second plane that is generally parallel to the first plane.

16. A system for correcting alignment of one or more vertebrae of a spine, comprising:
   first and second implants engageable to one of the one or more vertebrae, said first and second implants being configured for engagement with respective ones of first and second stabilization elements positionable along the spine; and
   a derotation instrument assembly including first and second elongated implant holders releasably engageable to respective ones of said first and second implants, wherein at least one of said implant holders includes a first arm and a second arm extending along a longitudinal axis with said first arm and said second arm pivotally coupled to one another for movement of proximal portions of said first and second arms relative to one another in a first plane including said longitudinal axis, said first and second arms each including a distal portion offset to a first side of said longitudinal axis and movable between a closed position in clamping engagement with a respective one of said first and second implants and an open position for releasing said respective implant, said derotation instrument assembly further including a transverse bridge positionable between and engageable to each of said first and second implant holders at a location spaced proximally from said first and second implants and proximally of said pivotal connection of said arms of said at least one implant holder, wherein said distal portions of said first and second arms of said at least one implant holder each extend along a second longitudinal axis and said distal portions lie in a second plane including said second longitudinal axis, said second plane being offset from and generally parallel to said first plane and said distal portions of said first and second arms move toward and away from one another in said second plane when said proximal portions of first and second arms are moved toward and away from one another in said first plane.

17. The system of claim 16, wherein each of said implant holders further comprises a derotation handle extending proximally from said location on each of said implant holders.

18. The system of claim 16, wherein said distal end portions further define an opening along one side thereof extending along the longitudinal axis that opens away from said longitudinal axis.

19. The system of claim 18, wherein said distal end portions are movable toward one another to grip said implant therebetween by pivoting a proximal end of said second arm toward said first arm.

20. The system of claim 19, wherein said distal end portions each include a projection extending toward the other of said distal end portions, said projection being received in detents in said implant when said implant holder is in said closed position.

21. The system of claim 16, wherein said at least one implant holder includes a latching mechanism for locking said first and second arms in said closed position.

22. The system of claim 21, wherein said proximal portions of said first and second arms define a receptacle therebetween, wherein said latching mechanism is located in said receptacle between said first and second arms and said latching mechanism includes a holding member mounted to said first arm with said holding member axially movable between said arms, said latching mechanism further including a latch member extending from said second arm that is releasably engageable to said holding member and as said proximal end of said second arm is moved toward said first arm said latch member axially displaces said holding member until a receptacle of said latch member aligns with said holding member, and said holding member is biased to move in a direction opposite said axial displacement to position said holding member in said aligned receptacle to maintain said first and second arms in said closed position.

23. The system of claim 22, further comprising a release button engaged with said holding member, said release button being operable to release said holding member from said latch member when said first and second arms are in said closed position to permit said arms to be moved to said open position thereby releasing said implant engaged between distal end portions of said first and second arms.

24. The system of claim 23, wherein said first and second arms are spring biased toward said open position.

25. The system of claim 16, wherein said first arm includes a length along said longitudinal axis that is greater than a length of said second arm along said longitudinal axis, wherein said first arm includes a receptacle at said location housing a pivotal ball member for engagement with a portion of said transverse bridge.

26. The system of claim 25, wherein said first arm includes a handle portion extending proximally from said location, and further comprising a locking member in said handle portion selectively engageable with said ball member to lock said ball member in position about said portion of said transverse bridge.

27. A method for assembling a system for correcting alignment of a spinal column of a patient, comprising:
engaging first and second implants to a first vertebra;
engaging a distal portion of respective first and second implant holders to respective ones of the first and second implants, the first and second implant holders each extending from the distal portion along a longitudinal axis to a proximal end outside the patient, wherein engaging the distal portion includes pivoting a proximal end of a first arm of the respective implant holder about a first joint of the respective implant holder toward a second arm of the respective implant holder to move a distal end of the first arm toward a distal end of the second arm and engage the respective implant between distal ends of the first and second arms; and
engaging a transverse bridge between each of the first and second implant holders at a location between distal and proximal ends of each of the first and second implant holders with each of the implant holders including a derotation handle extending proximally from the location and proximally from a proximal end of the second arm, wherein each of the locations includes a second joint spaced proximally from the first joint of the respective implant holder with the proximal end of the first arm being located between the first and second joints, and each of the second joints include a receptacle and a ball member pivotal in the receptacle, and engaging the transverse bridge includes positioning the transverse bridge through the ball members of the second joints.

28. The method of claim 27, further comprising manipulating the derotation handles to align the spinal column.

29. The method of claim 28, further comprising engaging elongate stabilization elements to each of the first and second anchors after aligning the spinal column to provide post-operative stabilization after manipulating the derotation handles to align the spinal column.

30. The method of claim 27, further comprising:
engaging third and fourth implants to a second vertebra;
engaging a distal portion of respective third and fourth implant holders to respective ones of the third and fourth implants, the third and fourth implant holders each extending from the distal portion thereof along a longitudinal axis to a location outside the patient, wherein each of the third and fourth implant holders includes a handle extending proximally from the location; and
engaging a second transverse bridge to the locations on each of the third and fourth implant holders.

31. The method of claim 30, further comprising engaging an inter-level linking assembly between the transverse bridges.

32. The method of claim 31, wherein each of the transverse bridges includes a clamping assembly and engaging the inter-level linking assembly includes clamping each of the clamping assemblies to an elongated link member of the linking assembly.

33. The method of claim 32, wherein the clamping assemblies are located at an end of the respective transverse bridges and further comprising:
securing at least one connector assembly to an end of at least one of the clamp assemblies; and
clamping the connector assembly to a second elongated link member.

34. The method of claim 27, wherein engaging the transverse bridge includes:
locking the connecting member in the joints.

35. The method of claim 27, wherein:
the first and second implants each include a receiver defining a proximally opening passage for receiving a respective one of first and second elongate stabilization elements positionable along the spinal column; and
engaging the distal portion of respective first and second implant holders includes clamping the distal portion along one side of the receiver so that the proximally opening passage remains substantially unobstructed for receiving the respective elongate stabilization element.

36. The method of claim 35, further comprising positioning at least one of the stabilization elements in the proximally opening passage of the receiver of at least one of the first and second implants with the respective implant holder engaged to the receiver.

37. The method of claim 35, wherein the first and second arms are movable toward and away from one another in a first plane including a longitudinal axis of the respective implant holder, wherein the distal portions are offset to one side of the longitudinal axis and are movable toward and away from one another in a second plane that is generally parallel to the first plane.

38. The method of claim 27, further comprising:

pivoting the ball member at the location of the first implant holder while positioning an elongate connecting member of the transverse bridge through the ball member; and locking the first ball member to the elongate connecting member of the transverse bridge by compressing the ball member about a relief in the ball member, wherein locking the first ball member includes threadingly advancing an elongate shaft of a locking member along an axial passage of the derotation handle to engage a distal end of the elongate shaft against the ball member.

39. The method of claim 38, further comprising:

pivoting the ball member at the location of the second implant holder while positioning the elongate connecting member of the transverse bridge through the second ball member; and locking the second ball member to the elongate connecting member of the transverse bridge.

40. The system of claim 16, wherein:

said first and second implant holders each include a ball member pivotally captured in a receptacle at said location thereof, each of said ball members including a passage extending therethrough;

said transverse bridge includes an elongated connecting member positioned through said passages in said ball members; and said first and second implant holders further each include a locking member operable to lock said ball member thereof in position in said receptacle about said connecting member, wherein said locking member including an elongated shaft positioned in an elongated axial passage of said handle, said locking member including a distal engaging end in said passage and is movable between a first position wherein said ball member is pivotal in said receptacle and a second position wherein said distal engaging end of said locking member engages said ball member in said receptacle and secures it in position therein.

41. The system of claim 1, wherein:

said first and second implant holders further each include a locking member operable to lock said ball member thereof in position in said receptacle about said connecting member.

* * * * *

UNITED STATES PATENT AND TRADEMARK OFFICE
CERTIFICATE OF CORRECTION

PATENT NO. : 7,655,008 B2
APPLICATION NO. : 11/350915
DATED : February 2, 2010
INVENTOR(S) : Lenke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this

Twenty-third Day of November, 2010

David J. Kappos
*Director of the United States Patent and Trademark Office*